United States Patent [19]

Grimsley et al.

[11] Patent Number: 5,439,441
[45] Date of Patent: Aug. 8, 1995

[54] SURGICAL INSUFFLATION SYSTEM WITH IMPROVED DETERMINATION OF BODY CAVITY PRESSURE

[75] Inventors: Richard L. Grimsley; Steven N. Carlisle, both of Cincinnati, Ohio

[73] Assignee: Snowden-Pencer, Inc., Tucker, Ga.

[21] Appl. No.: 134,460

[22] Filed: Oct. 12, 1993

[51] Int. Cl.⁶ ............................................. A61M 13/00
[52] U.S. Cl. ...................................... 604/26; 128/748
[58] Field of Search ................... 128/747, 748; 604/26

[56] References Cited

U.S. PATENT DOCUMENTS

| | | | |
|---|---|---|---|
| 4,676,774 | 6/1987 | Semm et al. | 128/748 |
| 4,874,362 | 10/1989 | Wiest et al. | 128/748 |
| 4,966,578 | 10/1990 | Baier et al. | 128/748 |
| 5,013,294 | 5/1991 | Baier | 604/26 |
| 5,047,010 | 9/1981 | Ams et al. | 128/748 |
| 5,246,419 | 9/1993 | Absten | 604/26 |

*Primary Examiner*—Max Hindenburg
*Attorney, Agent, or Firm*—Needle & Rosenberg

[57] ABSTRACT

Insufflation gas is introduced into a body cavity to be inflated. The gas flow is stopped, and the pressure in the body cavity is measured at plural, discrete intervals of time. Pressure reading values are stored in memory for a predetermined number n of the most recent pressure reading values. These stored pressure reading values are compared to one another to determine the pressure differential between the highest and lowest pressure values. New pressure readings are continually made at the time intervals, and the new pressure reading values replace the oldest pressure readings such that the most recent pressure reading values are stored in memory. Pressure measurements are continued if the maximum pressure differential in the predetermined number n of the most recent stored pressure reading values is less than the predetermined pressure differential. However, if the differential is less than a predetermined pressure differential, then it is determined that the pressure oscillations in the body cavity have subsided, and the nominal body cavity pressure is determined. If the measured pressure is below a preset target level of insufflation, additional gas may be introduced into the body cavity, and then pressure measurements may be resumed.

21 Claims, 4 Drawing Sheets

5,439,441

SURGICAL INSUFFLATION SYSTEM WITH IMPROVED DETERMINATION OF BODY CAVITY PRESSURE

BACKGROUND OF THE INVENTION

Endoscopic surgical techniques are becoming increasingly popular in order to avoid exposing patients to unnecessary risks and extended recovery times which result from traditional surgical techniques. During endoscopic surgery, using normal insufflation procedures, carbon dioxide gas typically is used to distend the abdominal cavity, peritoneum, or other body cavity, so that the surgical instruments and telescope can be inserted therein.

Carbon dioxide gas is supplied from a compressed gas cylinder and is regulated down from the typical tank pressure of about 880 PSI or higher to about one-half PSI for distending the body cavity. Care must be taken to avoid overinflating the body cavity and risking possible harm to the patient.

Gas is delivered into the body cavity, such as an interabdominal cavity, during insufflation by a flexible tube having a hollow needle at the end thereof. The inlet end of the flexible tube is connected to the output port of the insufflator. The flexible tube and the body cavity of the patient form an enclosed pressure vessel or system. This enclosed system is inflated with the pressurized gas when the insufflation apparatus determines that the body cavity pressure is below a preset target level. The injection of the gas to increase the pressure can cause the patient cavity system to exhibit pressure variations and oscillations. Such variations and oscillations occur for a time period after the gas flow has stopped.

FIG. 1(a) is a pressure versus time diagram showing a typical pressure profile measured at the output port of the insufflator during insufflation. The pressure is maintained high at the output port of the insufflator while the gas is being delivered to the body. Because of this higher local pressure at the output port, accurate body cavity pressure measurements cannot be made while the gas is flowing into the body cavity. Furthermore, since the body cavity pressure is measured through the same line in which the gas is supplied, pressure measurements can be made only after the gas flow is stopped. After the gas flow is stopped, the gas in the body cavity moves away from the output port of the insufflator and continues to fill the cavity until the pressure in the cavity stabilizes.

When the gas flow is terminated, the pressure in the body cavity, delivery system, tubing, etc., begins to oscillate, as shown in FIG. 1(a). The body cavity pressure oscillates around the actual cavity pressure with steadily decreasing amplitude on the oscillations until the pressure in the system stabilizes at the body cavity-pressure. When the oscillations subside, accurate pressure readings can be taken.

However, it takes a substantial period of time before the pressure stabilizes, enough so that accurate readings can be taken. If the pressure which is eventually measured is below the target inflation pressure, then additional gas must be introduced into the cavity, and the pressure measuring process must be repeated. The long waiting time required to allow the oscillations to subside is undesirable in that this increases the time required to complete the inflation. Also, during the surgical procedure, it is often necessary to continue to introduce gas into the body cavity, because of leakage and the like, in order to maintain the desired degree of inflation.

Thus, the waiting period while the pressure oscillations in the body cavity subside undesirably increases the time period of insufflation procedures. This increases surgical time and risk.

SUMMARY OF THE INVENTION

It is an object of this invention to provide a gas insufflation process and device which overcomes the disadvantages described above. Particularly, the process and apparatus in accordance with the invention provides a pressure regulating and measuring device which rapidly determines and controls the pressure in the body cavity. The process and apparatus in accordance with the invention rapidly determines when the pressure oscillations in the body cavity and the gas supply line have subsided, and then provides an accurate measurement of the nominal body cavity pressure.

The pressure measuring process in accordance with the invention includes introducing a gas into the body cavity to be inflated. When the gas flow stops, the pressure in the body cavity is measured at plural, discrete intervals of time. A predetermined number of the measured pressure reading values are stored in a memory device. A predetermined number n of the most recent stored pressure reading values are compared to one another to determine whether the differential between the highest and lowest pressure reading values is below a predetermined pressure differential. New pressure readings are continually made at the time intervals, and the new pressure reading values replace the oldest pressure reading values such that the most recent predetermined number of pressure reading values are stored in memory. Pressure measurements are continued while differences between the predetermined number n of the most recent stored pressure reading values are not below the predetermined pressure differential. When differences between the n most recent stored pressure reading values become less than a predetermined pressure differential, signifying that the pressure oscillations in the body cavity have subsided, the nominal body cavity pressure is determined. The nominal body cavity pressure may be determined as an average of all or a predetermined number n' of the most recent stored pressure reading values. If the nominal body cavity pressure is below the target pressure of insufflation, additional gas may be introduced into the body cavity, and then pressure measurements may be resumed as described above.

The insufflation device in accordance with the invention includes a gas supply means for introducing a gas into a body cavity to be inflated. A control means for controlling pressure in the body cavity includes a device such as an electronic pressure transducer for measuring the pressure in the body cavity at plural discrete intervals of time, when no gas is being introduced into the body cavity. A memory means stores the measured pressure reading values. A comparing device is provided to determine the pressure differential between highest and lowest pressures in a predetermined number n of the most recent stored pressure reading values. Pressure measurements are continued if this pressure differential is not less than the predetermined pressure differential. A means is provided for determining a nominal body cavity pressure when the pressure differential becomes less than the predetermined pressure differential.

BRIEF DESCRIPTION OF THE DRAWINGS

The invention will now be described in conjunction with the attached drawings wherein.

DETAILED DESCRIPTION OF THE INVENTION

Figure 1A:
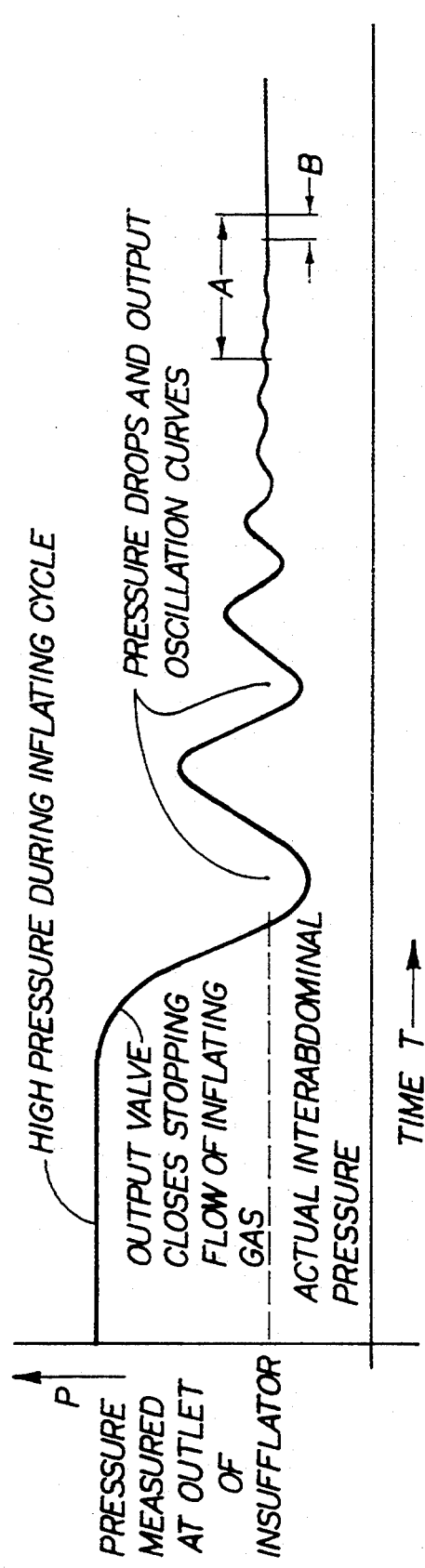
FIG. 1(a) is a timing diagram illustrating the pressure in the body cavity and at the output port of the insufflator during an inflation cycle.

The apparatus in accordance with the invention relates to an insufflation device, having an appropriate pressure regulating device for measuring and controlling the pressure in the body cavity of a patient during insufflation. The apparatus includes a gas supply device for introducing a gas into a body cavity to be inflated. This gas supply may include a compressed gas source, a flexible tube, a hollow needle, or any other suitable gas supplying device.

A pressure regulating device is included to determine and control the pressure in the body cavity. This pressure regulating device may include appropriate computer software and hardware to function in the manner to be described in more detail hereinafter. The pressure regulating device includes a detector for measuring the pressure in the body cavity at plural, discrete intervals of time, when no gas is being introduced into the body cavity. In the preferred embodiment of the invention, the detector is an electronic pressure transducer.

A memory is provided for storing pressure reading values for a predetermined number of the measured pressure reading values in the body cavity. A comparator device is included for comparing the differences between the pressure reading values to determine whether the pressure reading values fall below a predetermined pressure differential. This comparing function may be performed in a computer memory or by a comparator circuit.

Pressure measurements are continued at the discrete intervals if the differential between the highest and lowest pressures in a predetermined number n of the most recent stored pressure reading values is not less than the predetermined pressure differential. However, when all or a predetermined percentage (e.g., 80 or 90%) of the pressure reading values become less than the predetermined pressure differential, it is determined that the pressure in the body cavity system has become stabilized enough so that accurate pressure readings can be taken. The measured value for the body cavity system is determined as being the nominal body cavity pressure at the time when the pressure has stabilized. This nominal body cavity pressure may be considered to be equal to an average of all or a predetermined number n' of the most recent pressure reading values, such as an average of the last four or eight pressure reading values stored in the memory. Alternatively, the nominal body cavity may be considered to be the last measured pressure value.

Preferably, the pressure regulating device controls the pressure measuring device so as to take pressure measurements in the body cavity at about 0.5 milliseconds intervals. Any number of pressure measurements can be stored in the memory, but preferably, at least the most recent ten pressure reading values, and preferably the most recent 32 pressure reading values are stored. This would mean that the regulating device in conjunction with the pressure measuring device had determined that the pressure in the system had been stable for no more than 16 milliseconds after it had become stable.

Any appropriate display means may be used for displaying the nominal body cavity pressure. For example, the display means may be an electronic display, such as in a digital (computer) implementation, or the value may be displayed by means of a gauge or other physically activated (analog) display. Examples of appropriate displays include a light emitting diode display, a liquid crystal display, an analog needle gauge display, a computer monitor, paper printout display, or an ink and pen tracing display.

The invention further relates to a process for measuring pressure in a body cavity during insufflation thereof, for example, during endoscopic surgical techniques. The process includes introducing a gas into the body cavity to be inflated, for example by a hollow needle connected to a compressed gas supply via a flexible tube. The pressure of the gas supply is properly reduced to a suitable level before it is introduced into the body. When the introduction of gas into the body cavity is discontinued, gas pressure measurements in the body cavity are taken at plural, discrete intervals of time.

The measured pressure values are stored in a memory device as pressure reading values for a predetermined number of the measured pressure readings. For example, the pressure measurements can be made every 0.5 milliseconds, and only a predetermined number (e.g., 32) of the most recently measured values need be stored. Thus, a bubble type memory system may be used, wherein, as new measurements are taken, the memory elevates each prior measurement up one notch, and discards the oldest measurement in memory. Thus, the pressure reading values are discarded in a "first in, first out" (FIFO) manner. The comparison step may be initiated when the predetermined number n of pressure reading values corresponds to a completely full bubble-type memory (i.e., n=32 pressure reading values), or it may begin when the number of pressure reading values exceeds a lower level (e.g., $32 \geq n \geq 10$ pressure reading values), while the bubble type memory initially is being filled.

The differences between a predetermined number n of the most recent pressure reading values are compared to determine the pressure differential between the highest and lowest pressure reading values. A certain minimum number of pressure reading values must be stored in memory before it is determined whether this pressure differential is less than a predetermined value. At least two pressure readings must be taken, but preferably at least 10 pressure readings are taken before it is determined whether the differential between the stored pressure reading values falls below the predetermined pressure differential. Taking at least ten readings prevents coincidental and erroneous determinations that the pressure in the body cavity has stabilized.

If the differences between the predetermined number n of the most recent stored pressure reading values are not below the predetermined pressure differential, then pressure readings are continued. Howevers, if the maximum difference within the predetermined number n of the most recent stored pressure reading values is below the predetermined pressure differential, the process determines that the pressure in the body cavity has stabilized. In this case, a nominal body cavity pressure is determined. This nominal body cavity pressure may be taken as a mathematical average of a predetermined number n' of the most recent pressure reading values, such as the last four or eight pressure reading values, or it may be taken as an average of all of the predetermined number n of the most recent pressure reading values.

In a preferred embodiment of the process in accordance with the invention, the predetermined number of pressure reading values, n, stored in memory is at least the last ten pressure reading values. Even more preferably, n is equal to the last 32 pressure reading values are stored in the memory.

The predetermined pressure differential below which the differences between the stored pressure reading values must fall may be adjusted and set by the skilled practitioner, based on experience, final target insufflation pressure, type of cavity being inflated, and the like. For insufflating the interabdominal cavity, in the preferred embodiment of the invention, this predetermined pressure differential is about 1 mm Hg. In other words, if the highest stored pressure reading value minus the lowest stored pressure reading value is less than 1 mm Hg, then it is determined that the pressure oscillations have subsided and that the gas pressure in the body cavity has stabilized. The nominal body cavity pressure can then be determined.

The nominal body cavity pressure may be taken as equal to an average of some or all of the predetermined number of the pressure reading values. In a preferred embodiment of the invention, the nominal body cavity pressure is equal to the average of the last eight pressure reading values stored in memory (i.e., n' is equal to eight).

The process in accordance with the invention may include a step for indicating the nominal body cavity pressure on a display. Any suitable display device known in the art can be used without departing from the invention.

In a particularly preferred embodiment of the process in accordance with the invention, if it is determined that the nominal body cavity pressure is below a target pressure level for the body cavity, after the pressure has stabilized and accurate measurements are taken as discussed above, then the introduction of gas into the body cavity is resumed for a period of time, as determined by a proportional integral derivative (PID) loop, and pressure measurements are repeated. The process of inflating, measuring, and comparing the pressure to a target pressure may be repeated until the pressure in the body cavity is equal to the target pressure level (or within a suitable range from this target level).

The following is a description of a preferred embodiment of the invention corresponding to the attached drawings.

As discussed in the Background portion of this application, FIG. 1(a) shows typical pressure fluctuations present in the body cavity system (i.e., including the patient body cavity, the flexible tube and the gas flow channels in the insufflation apparatus leading to the pressure measuring device), measured at the output port of the insufflator. As the insufflator is inflating the body cavity, the pressure near the output port of the insufflation device is typically high relative to the pressures in the body cavity. When the delivery of gas is terminated, the pressure in the cavity (and also in the gas supply line which is in communication with the body cavity) begins to oscillate as it stabilizes. The oscillations decrease in amplitude over time.

The apparatus in accordance with the invention rapidly determines when the pressure oscillations in the system have subsided such that accurate pressure readings can be taken. As shown in FIG. 1(a), when the pressure oscillations have subsided such that the maximum differential within a predetermined number of pressure readings falls below a predetermined pressure differential (region "A" in FIG. 1(a)), the apparatus and process in accordance with the invention determines that accurate pressure readings can be taken. The finally determined nominal body cavity pressure may be taken as an average of a predetermined number of pressure readings, such as an average of the pressure readings in region "B", contained within region "A" in FIG. 1(a).

Figure 1B:
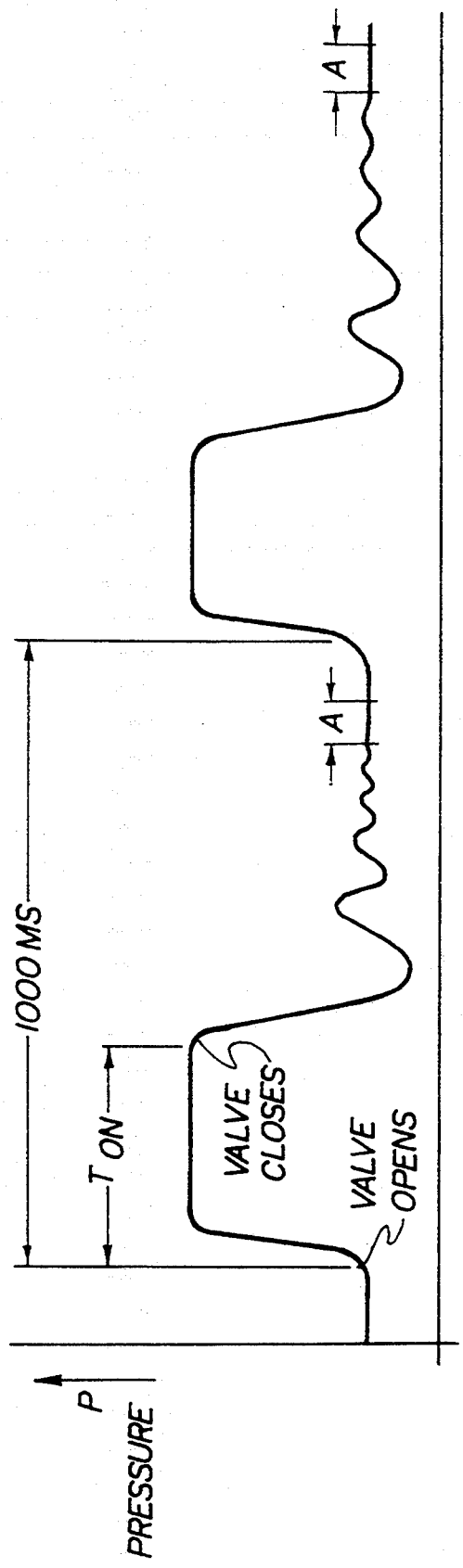
FIG. 1(b) is a timing diagram illustrating the pressure in the gas supply line during two inflation cycles.

FIG. 1(b) is a timing diagram illustrating the pressure in the system during two predetermined inflation cycle periods. A typical inflation cycle period (i.e., the time period between opening the solenoid valve) may be 1000 milliseconds. Prior to delivering gas, a proportional integral derivative (PID) loop determines how long the valve should remain open to achieve a certain level of inflation for the cavity ($\tau_{on}$). After the valve closes, pressure measurements are made until an accurate nominal body cavity pressure can be determined (region "A", corresponding also to region "A" in FIG. 1(a)). After the pressure measurements are made, a venting device may be activated (if necessary), and the remainder of the predetermined cycle period runs. Based on the determined nominal body cavity pressure, a new valve open time ($\tau_{on}$) may be determined by the PID loop, and the valve may be again opened to resume inflation of the body cavity, as shown in FIG. 1(b).

Figure 2:
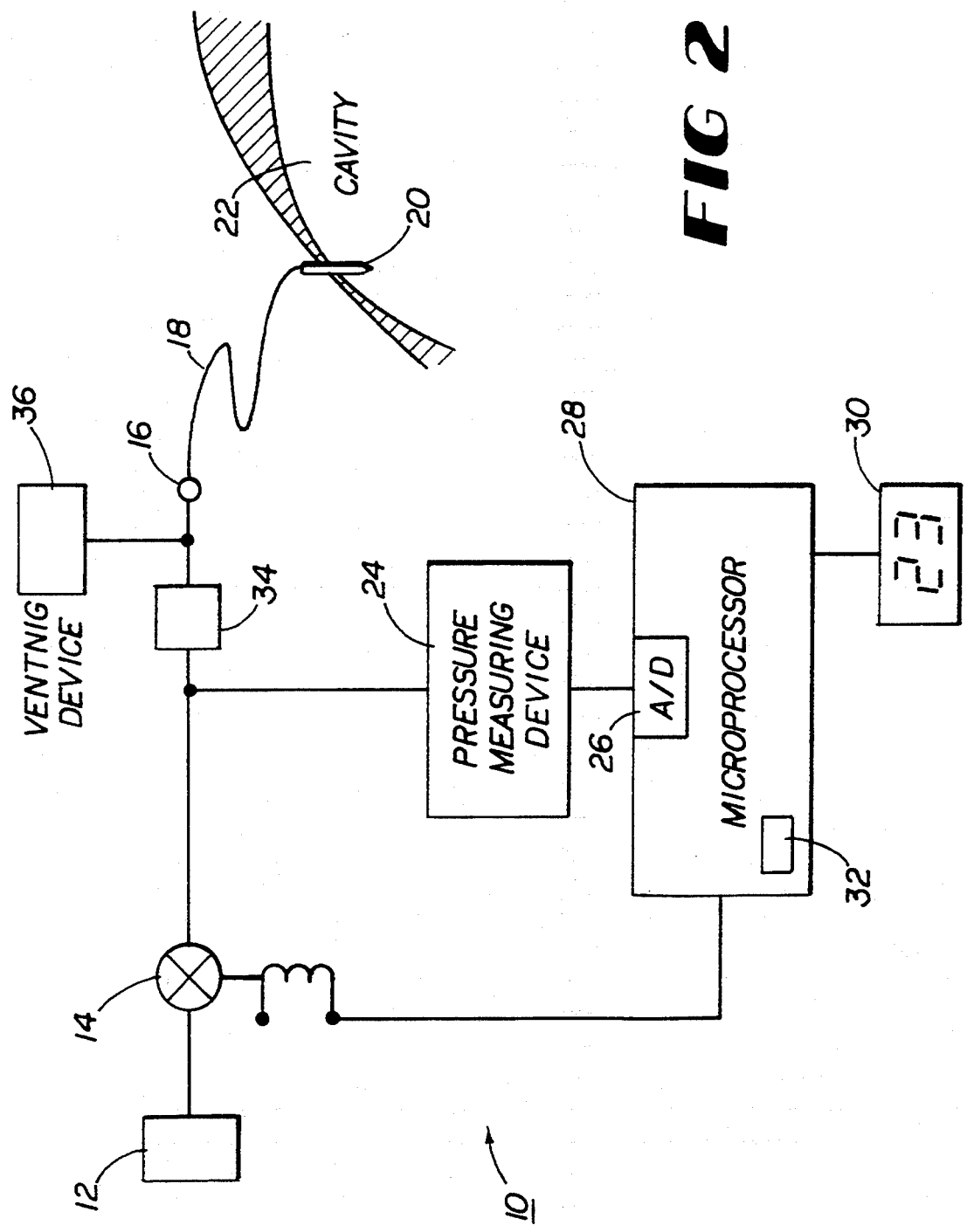
FIG. 2 is a schematic diagram illustrating the apparatus in accordance with the invention.
Figure 3:
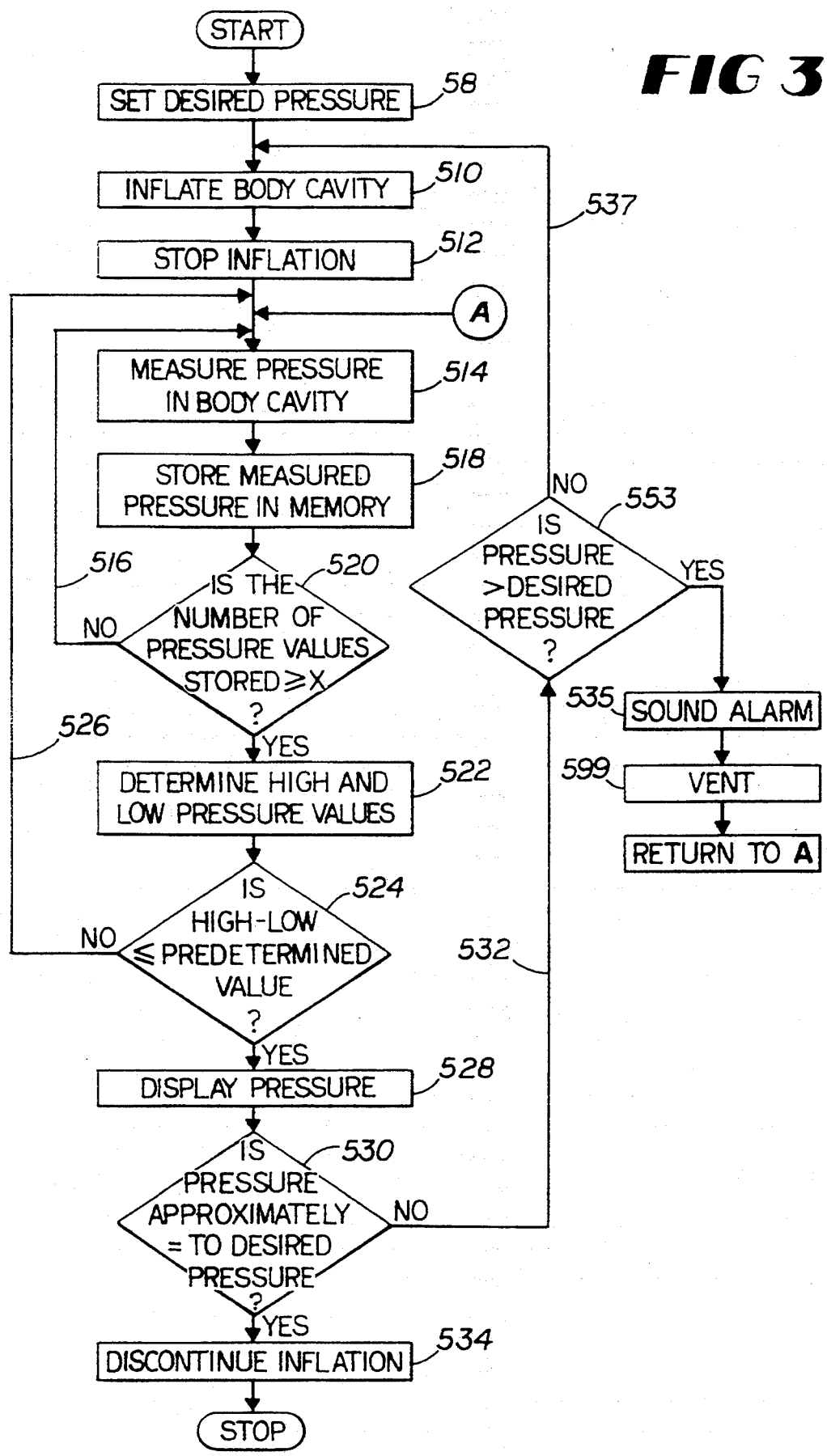
FIGS. 3 and 4 are flow diagrams illustrating the process in accordance with the invention.

The apparatus in accordance with the invention is shown generally at reference number 10 in FIG. 2. The apparatus and process in accordance with the invention will be described in conjunction with FIGS. 2–4. Reference numbers proceeded by the letter "S" refer to steps shown in the flow diagrams of FIGS. 3 and 4.

Carbon dioxide ($CO_2$) or other suitable insufflation gas is supplied from a compressed gas cylinder 12 to inflate body cavity 22 (S10). The solenoid valve 14 remains open for a predetermined inflation period ($\tau_{on}$) determined by the PID loop. Appropriate pressure regulators may be included so as to reduce the pressure from the typical tank pressure (about 880 PSI) to about 0.5 PSI for insufflating the body cavity. An electrically activated solenoid valve 14 is present to enable control of the gas flow into the body cavity.

Because of the reduction in pressure, the gas from the gas supply 12 will also undergo a corresponding reduction in temperature. In one particularly preferred embodiment of this invention, a gas heater 34 is provided to heat the gas to a temperature at or about the body temperature of the patient. Preferably, the heater 34 is a flat plate heater of the type described in copending and concurrently filed U.S. patent application Ser. No. 08/134,458 entitled "GAS HEATING DEVICE FOR ENDOSCOPIC SURGERY" to Richard Grimsley and Gary Mixon, which application is entirely incorporated herein by reference.

The solenoid valve 14 may be included in a housing (not shown) of the insufflation device 10, with an appropriate output port 16 for connecting with one end of a flexible vinyl tube 18. The opposite end of the tube 18 is connected to a hollow needle 20 which is inserted into a body cavity 22 of a patient for insufflation.

The output port 16 of the insufflation device is connected to a pressure measuring device 24 which is used to determine the pressure in the body cavity. The pressure measuring device 24 may be an electronic pressure transducer. Because the gas is being fed into the body cavity through the same line in which the pressure measurements are made, pressure in the body cavity can only be measured at a time when the gas flow is stopped. Also, accurate pressure measurements can be made only after the oscillations in the body cavity and the gas supply line have subsided.

The apparatus and process according to the invention allows insufflator 10 to monitor the pressure in the cavity 22 to determine when it has stabilized enough so that an accurate reading can be made. The invention allows insufflator 10 to measure the body cavity pressure as soon as it is stabilized, thereby minimizing the time required for pressure measurement, and reducing the overall time of the surgical procedure.

When solenoid valve 14 closes, the inflation of body cavity 22 is stopped (S12). The pressure transducer 24 is activated to take pressure measurements. (S14) at discrete intervals, such as every 0.5 milliseconds. The output of the electronic pressure transducer 24 is a voltage that is proportional to the pressure in the tube 18 going into the body cavity 22. The transducer 24 output is converted into a digital signal by an analog to digital (A/D) converter 26 and input as data into a microprocessor 28. These pressure measurements are stored in a memory (S18) in the microprocessor 28. The memory is adapted so as to store a predetermined number of the most recent pressure measurements such that as a new measurement is stored, the oldest measurement remaining in the memory is no longer stored. In this way, the pressure oscillations as a function of time are stored. As a preferred example, 32 readings are stored (S20), although it is not necessary for the memory to be completely full before the stability of the pressure oscillations is checked. In other words, although the memory may hold the most recent 32 pressure reading values when completely full, the device could begin to check whether the pressure differential value is below a predetermined value after fewer than 32 values are stored, such as, after the value X is 10 in Step S20 in FIGS. 3 and 4. If the memory does not include enough pressure value readings, the process returns (S16) to take additional readings.

If the differential among the last "X" measurements stored in memory is not less than a predetermined pressure differential, e.g., if the largest stored pressure reading value minus the lowest stored pressure reading value is greater than 1 mm Hg (S22 and S24), then the process returns (S26) to take another pressure measurement at S14. However, if the differential among the last "X" measurements is less than the predetermined pressure differential (e.g., if the largest stored pressure reading value minus the lowest stored pressure reading value is less than or equal to 1 mm Hg (S22 and S24)), the pressure regulating and controlling device determines that the pressure in the body cavity has stabilized. The controller then determines the nominal body cavity pressure and displays the nominal body cavity pressure on a pressure display 30 (S28). The controller has a target pressure input device 32 so as to enable the operator to set a target pressure for the insufflation (S8). This target pressure is set before the insufflation process begins.

By setting a target pressure at Step S8, the controller determines an estimated solenoid valve 14 open time, based on the gas flow rate, cavity size, and the like. The apparatus in accordance with the invention begins insufflation, while periodically stopping to check the pressure via the pressure transducer 24. In a particularly preferred embodiment of the invention, the pressure in the body cavity may be measured with the apparatus including an independent pressure sensing port, such as that described in U.S. patent application Ser. No. 08/134,459, entitled "SURGICAL INSUFFLATOR WITH SEPARATE PRESSURE SENSING PORT", to Richard Grimsley, filed concurrently herewith. This application is entirely incorporated herein by reference.

The nominal body cavity pressure displayed on the display 30 may be computed in a variety of different manners. For example, the display may show an average of the last four or eight measured values (i.e., n'=4 or 8). Alternatively, the output may display an average of any number of the stored values, or it may even display simply the last measured value.

The device in accordance with the invention checks to determine if the nominal body cavity pressure is within a predetermined range (e.g., ±0.2 mm Hg) of the target pressure set at the target pressure input device 32 (S30). If the pressure is not at the target level (S32), the controller checks to determined if the nominal body cavity pressure is greater than the target pressure (S33). If the nominal body cavity pressure is too high, an alarm may be activated (S35), and a venting device 36 (S99) may be activated to relieve pressure in the system. Then, the apparatus may be returned to again measure the pressure in the body cavity S14. If the nominal body cavity pressure is below the target pressure as measured at S33, then the process returns (S37) such that the solenoid valve 14 is opened (S10) to allow more gas to enter the body cavity 22. If the nominal body cavity pressure has reached the target level at S30, insufflation is discontinued (S34). Control passes back to "A" in FIG. 3, to maintain the pressure.

Figure 4:
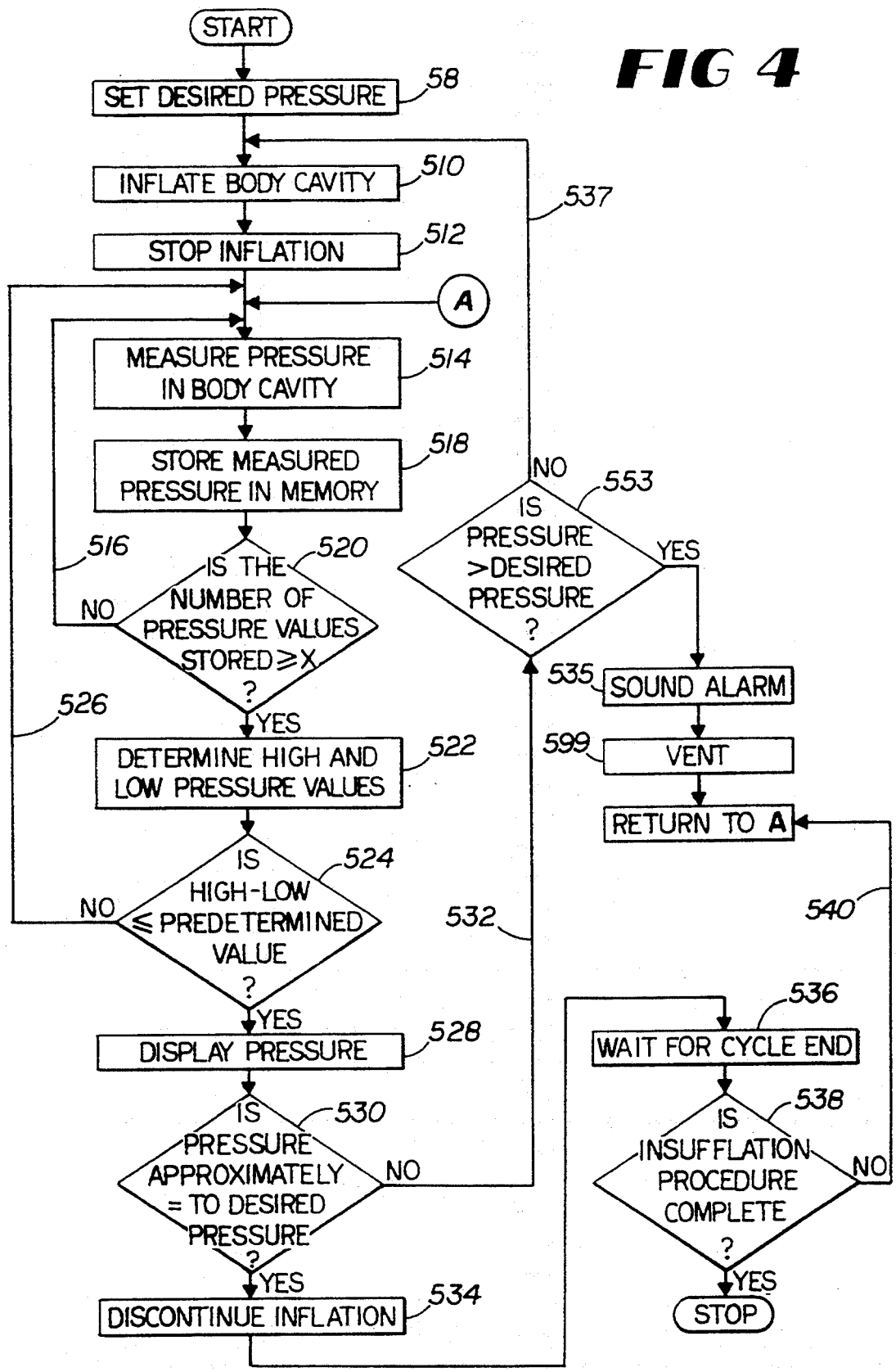

As further shown in FIG. 4, the apparatus in accordance with the invention is capable of automatically controlling the pressure to maintain the target pressure level. After the target pressure is attained, the apparatus discontinues inflating the cavity 22 for the remainder of a predetermined cycle period (S36). After the predetermined inflation cycle period has expired, the apparatus checks whether the insufflation procedure is completed (S38). If the insufflation procedure is continuing, the apparatus returns (S40) to again check the nominal body cavity pressure (S14). If, due to leakage or the like, the nominal body cavity pressure has fallen below the target level, a new valve open time is calculated by the PID loop, and the apparatus will begin to automatically reinflate the cavity.

Alternatively, an override may be provided with the apparatus in accordance with the invention so as to enable the operator to manage the body cavity pressure manually.

While the invention has been described in terms of its preferred embodiment, those skilled in the art will appreciate that various modifications and changes may be made without departing from the spirit and scope of the invention, as defined in the appended claims.

I claim:

1. A process for supplying insufflation gas to inflate a body cavity of a patient during an endoscopic procedure, comprising the steps of:
   supplying insufflation gas into the body cavity;
   discontinuing the supply of gas into the body cavity;
   measuring pressure in communication with the body cavity to obtain pressure reading values taken at plural discrete intervals of time when no gas is being introduced into the body cavity to obtain a plurality of pressure reading values;
   storing a plurality of said pressure reading values;
   comparing a predetermined number n of the most recent pressure reading values to determine the pressure differential between a highest and a lowest pressure reading value therein;
   determining a nominal body cavity pressure when said pressure differential becomes less than a predetermined pressure differential.

2. A process according to claim 1, wherein the pressure is measured by an electronic pressure transducer.

3. A process according to claim 1, wherein the discrete intervals of time are about 0.5 milliseconds.

4. A process according to claim 1, wherein the predetermined number n of pressure reading values is at least 10.

5. A process according to claim 4, wherein the number n of pressure reading values is 32.

6. A process according to claim 1, wherein the predetermined pressure differential is about 1 mm Hg.

7. A process according to claim 1, wherein the step of determining nominal body cavity pressure is performed by averaging a predetermined number n' of the most recent pressure reading values.

8. A process according to claim 7, wherein n' is less than n.

9. A process according to claim 1, further including the step of indicating the nominal body cavity pressure on a display.

10. A process according to claim 1, wherein the measuring step is performed at least eight times, and the last eight pressure reading values stored in memory are averaged to determine the nominal body cavity pressure.

11. A process according to claim 1, further including the step of resuming the supply of gas into the body cavity when the nominal body cavity pressure is less than a target pressure value.

12. Insufflation apparatus for supplying insufflation gas to inflate a body cavity of a patient during an endoscopic procedure, comprising:
   supply means for supplying insufflation gas into said body cavity;
   control means for controlling the pressure in the body cavity, said control means including pressure measuring means in communication with the body cavity for providing pressure reading values taken at discrete intervals of time when no gas is being introduced into the body cavity;
   memory means for storing said pressure reading values;
   means for comparing a number n of the most recent pressure reading values to determine the differential between a highest and a lowest pressure reading value therein; and,
   means for determining a nominal body cavity pressure when said differential becomes less than a predetermined pressure differential.

13. Insufflation apparatus according to claim 12, wherein the pressure measuring means includes an electronic pressure transducer.

14. Insufflation apparatus according to claim 12, wherein the pressure measuring means provides pressure reading values at intervals of about 0.5 millisecond.

15. Insufflation apparatus according to claim 12, wherein the number n of the most recent pressure values is at least 10.

16. Insufflation apparatus according to claim 15, wherein the value of n is 32.

17. Insufflation apparatus according to claim 12, wherein the predetermined pressure differential is about 1 mm Hg.

18. Insufflation apparatus according to claim 12, wherein the means for determining the nominal body cavity pressure calculates an average of a predetermined number n' of the most recent pressure reading values.

19. Insufflation apparatus according to claim 18, wherein n' is less than n.

20. Insufflation apparatus according to claim 12, including means for indicating the nominal body cavity pressure, said indicating means being selected from the group consisting of: a light emitting diode display, a liquid crystal display, an analog needle gauge display, a computer screen, a paper printout, and an ink and pen tracing display.

21. Insufflation apparatus according to claim 12, further including means for resuming the supply of gas into the body cavity when the nominal body cavity pressure becomes less than a predetermined target pressure.

* * * * *